United States Patent [19]

Nishikawa et al.

[11] Patent Number: 4,994,374

[45] Date of Patent: Feb. 19, 1991

[54] DIAGNOSTIC METHOD OF CIRRHOSIS AND HEPATIC CANCER

[75] Inventors: Atsushi Nishikawa; Naoyuki Taniguchi, both of Osaka; Isamu Takagahara, Hyogo, all of Japan

[73] Assignee: Oriental Yeast Co., Ltd., Tokyo, Japan

[21] Appl. No.: 362,414

[22] PCT Filed: Sep. 6, 1988

[86] PCT No.: PCT/JP88/00898

§ 371 Date: May 1, 1989

§ 102(e) Date: May 1, 1989

[87] PCT Pub. No.: WO89/02474

PCT Pub. Date: Mar. 23, 1989

[30] Foreign Application Priority Data

Sep. 7, 1987 [JP] Japan .................. 62-221992

[51] Int. Cl.$^5$ .................. C12Q 1/48; A61K 37/52; A61K 35/16

[52] U.S. Cl. .................. 435/15; 435/14; 424/9; 424/945; 424/531; 424/553

[58] Field of Search .................. 435/14, 15, 4; 424/52, 424/95, 99, 104, 106, 94.5

[56] References Cited

FOREIGN PATENT DOCUMENTS 0272603 6/1988 European Pat. Off. .

OTHER PUBLICATIONS

The Levels of Nucleotide-Sugar: Glycoprotein Sialyl- -and N-Acetyl Glucosaminyl-Transferases in Normal and Pathological Human Sera., Mookerjea et al, Can. J. Biochem. 50, 738–740 (1972).

Glycosyl Transferase and Glycosidase Activities in Ovarian Cancer Patients, Chatterjee et al., Cancer Res. 39, 1943 (1979).

Studies on VDP-N-Acetyl Glucosamine: α Mannoside β-N-Acetyl-Glucosaminyl Transferase of Rat Liver Hepatomas, Miyagi et al., BBA 661, 148 (1981).

Serum Levels of Glycosyltransferases . . . Weiser et al., CRC Critical Reviews in Clinical Lab Sciences.

Primary Examiner—Merrell C. Cashion, Jr.
Assistant Examiner—G. S. Kishore
Attorney, Agent, or Firm—Browdy and Neimark

[57] ABSTRACT

This invention relates to a method of diagnosing cancerous diseases, which comprises measuring the amount of UDP-N-acetylglucosamine:glycoprotein N-acetylglucosaminyl-transferase in body fluid and evaluating the increase in its amount for the diagnosis of hepatic diseases.

AFP, CEA and γ-glutamyltranspeptidase have hitherto been used as tumor markers for the diagnosis of hepatic cancer. But these conventional tumor markers show a positivity rate of about 60%, making early diagnosis almost impossible.

The method of this invention employs UDP-N-acetylglucosamine:glycoprotein N-acetylglucosaminyl-transferase as tumor marker, whereby early diagnosis of hepatic cancer can be made almost completely.

1 Claim, No Drawings

DIAGNOSTIC METHOD OF CIRRHOSIS AND HEPATIC CANCER

FIELD OF THE INVENTION

This invention relates to a method of diagnosing cancerous diseases.

More particularly, it relates to a method of diagnosing cancerous diseases of the liver, etc. based on the increase in the amount of UDP-N-acetyl-glucosamine:-glycoprotein N-acetylglucosaminyltransferase III (hereinafter abbreviated a Gn-T-III ) in body fluid.

The method of this invention allows simple diagnosis of cancerous diseases such as hepatic cancer (hepatocirrhosis) by measuring the increase in the amount of Gn-T-III in body fluid ( e.g., serum, saliva and urine ), and hence will be of much benefit to the medical and diagnostic fields.

PRIOR ART AND PROBLEMS TO BE SOLVED BY THE INVENTION

GOT, GPT, LDH, ChE and many other test items have been adopted for general diagnosis of hepatic functions.

These test items, however, are no more than to check the comparative degree of hepatic functions, and are far from direct diagnosis of hepatic diseases, particularly hepatic cancer.

Measurement of tumor markers, such as AFP and CEA, is also known to be necessary for the diagnosis of hepatic cancer and has been put into practice.

But these conventional tumor markers show a positivity rate of 60 % at the highest, making early diagnosis almost impossible.

Recently, γ-glutamyltranspeptidase is receiving attention as a new tumor marker (particularly for hepatic cancer), because of the new fact that the blood of patients with hepatic cancer contains glycoproteins carrying different sugar-chain structure compared with normal subjects. However, this γ-glutamyltranspeptidase is not better than AFP, CEA and others as a tumor marker.

MEANS TO SOLVE THE PROBLEMS

Detailed studies on the change in sugar-chain structure in patients with hepatic cancer revealed that N-acetylglucosamine is attached, through β1,4-linkage, to the mannose (of β-1,4-linkage) bound to the trimannosyl core of sugar chain of asparagine linked type. We continued our investigation on the assumption that this change might be accompanied by the increase in the amount of Gn-T-III—an enzyme capable of transferring this N-acetylglucosamine. As a result, it was demonstrated that the sera of patients suffering hepatic diseases (particularly hepatic cancer) show a significantly higher Gn-T-III activity compared with normal subjects. We then succeeded in establishing a simple method for measuring the amount of this enzyme. The present invention was accomplished on the basis of these findings.

It was first found by the present inventors that the sera of normal subJects generally show a Gn-T-III activity as low as about 2.0±0.5 nmol/ml/h, while the sera of patients with hepatic cancer have about 2 to 3 times the activity, the sera of patients with hepatocirrhosis about 1.5 times and the sera of patients with chronic hepatitis 1.2 times.

On page 634 of Preliminary Notes for the 60th Meeting of Japanese Biochemical Society, is described a method of measuring Gn-T-III activity, in which N-acetylglucosamine is transferred to GnGn sugar chain and the product thus formed is measured by high-performance liquid chromatography. However, it is not known at all to apply this method to the diagnosis of cancerous diseases.

In the method of this invention, the amount of Gn-T-III is preferably measured by allowing it to act upon uridine diphospho N-acetylglucosamine (hereinafter abbreviated as UDP-GlcNAc) and to transfer N-acetylglucosamine to GnGn sugar chain. Thus the product formed is detected by high-performance liquid chromatography. In this case, if the GnGn sugar chain is previously fluorescence-labelled, the product can be easily detected by monitoring the fluorescence intensity. The GnGn sugar chain used in this invention is isolated from human transferrin, and then pyridylaminated (fluorescence labelling) by the method of Hase et al. (S. Hase et al, Journal of Biochemistry, 197–203 (1984), as shown by formula (I).

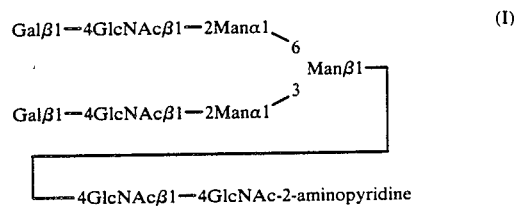

β-Galactosidase is then allowed to act upon this sugar chain, giving pyridylaminated GnGn sugar chain of formula (II).

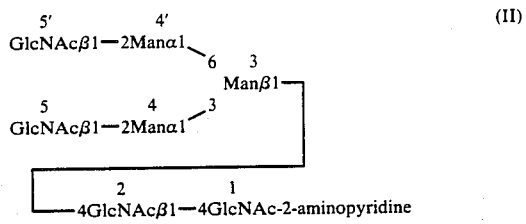

The GnGn sugar chain herein means the part of compound (II) from which 2-aminopyridine (fluorescent substance) is removed, and it also includes a derivative thereof in which fucose is attached to the 1-position (GlcNAc).

The reaction of Gn-T-III in the method of this invention is shown by the following equation (III):

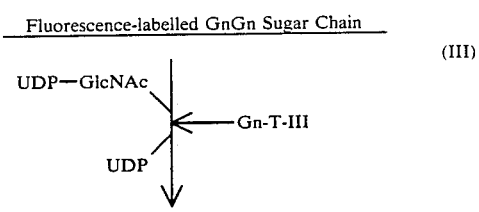

-continued
Fluorescence-labelled GnGn Sugar Chain

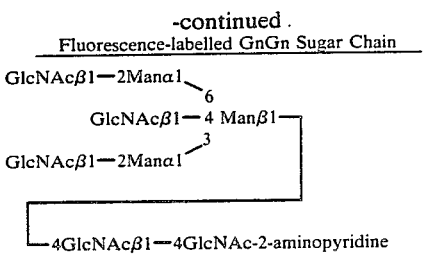

The reaction mixture was subjected to high-performance liquid chromatography, and the amount of reaction product was determined from the fluorescence-intensity, thus measuring the enzyme activity of Gn-T-III.

The amount of Gn-T-III may also be measured by other methods, such as by the antigen-antibody reaction.

EFFECTS ACHIEVED BY THE INVENTION

It was demonstrated that hepatic disease increases the Gn-T-III activity in the serum, and that this enzyme activity can be easily measured by allowing it to act upon UDP-ClcNAc to transfer N-acetylglucosamine to GnGn sugar chain and determining the amount of reaction product by high-performance liquid chromatography. This invention provides a simple method for diagnosing cancerous diseases such as hepatic cancer based on these findings.

Presented below is an Example of this invention.

EXAMPLE

| Reagent | |
|---|---|
| 250 mM | MES (2-(N-morpholino)ethanesulfonic acid monohydrate) (pH: 6.25) |
| 400 mM | GlcNAc (N-Acetylglucosamine) |
| 20 mM | $MnCl_2$ |
| 40 mM | UDP-GlcNAc |
| 1.0% | Triton X-100 |
| 150 μM | GnGn sugar chain (flurorescence-labelled) |

Into fifty containers each containing 50 μl of the above reagent, were added 50 μl of sera taken from patients with primary hepatic cancer, patients with hepatocirrhosis, patients with chronic hepatitis, patients with fatty liver and normal persons (1 cases each), the mixtures were incubated at 37° C. for one hour, and the reaction was terminated by adding 20 μl each of a solution containing 0.2M EDTA and 0.1M sodium borate.

Each of the reaction mixtures (1 μl) was subjected to high-performance liquid chromatography, fluorescene-intensity chromatograms were prepared, and the Gn-T-III relative activity was determined for each case.

The result is shown in Table 1 below.

TABLE 1

| | Gn-T-III Relative Activity |
|---|---|
| Serum of patients with primary hepatic cancer (n mol/n/ml serum) | 3.7 ± 2.3 |
| Serum of patients with hepato-cirrhosis | 3.3 ± 1.8 |
| Serum of patients with chronic hepatitis | 2.0 ± 0.5 |
| Serum of patients with fatty liver | 2.0 ± 0.5 |
| Serum of normal persons | 2.0 ± 0.5 |

What is claimed is:

1. A method for diagnosing hepatocirrhosis or hepatic cancer which comprises the following steps:
   (a) adding fluorescence-labelled GnGn sugar chain and UDP-GlcNAc to a serum sample to react with UDP-N-acetylglucosamine:glycoprotein N-acetyl-clucosaminyltransferase III (Gn-T-III) in said serum sample to produce the following compound:

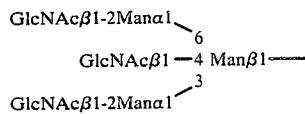

(b) subjecting the resulting reaction solution containing said compound to high-performance liquid chromatography; and
   (c) examining the increase in degree of Gn-T-III activity.